United States Patent
Ryklina et al.

(10) Patent No.: US 10,080,489 B2
(45) Date of Patent: Sep. 25, 2018

(54) METHOD OF SURGICAL TREATMENT OF INTESTINAL OBSTRUCTIONS IN NARROW AND LARGE INTESTINE AND DEVICE FOR ITS IMPLEMENTATION

(71) Applicants: Globetek 2000 Pty Ltd, Brighton (AU); The Federal State Autonomous Educational Institution of the Higher Professional Education National, Moscow (RU)

(72) Inventors: Elena Prokopievna Ryklina, Moscow (RU); Victor Mikhailovich Suturin, Melbourne (AU); Sergey Dmitrievich Prokoshkin, Moscow (RU); Mikhail Vladimirovich Soutorine, Melbourne (AU); Irina Yurievna Khmelevskaya, Moscow (RU); Artem Nikolaevich Chernov-Kharaev, Moscow (RU); Andrey Viktorovich Korotitskiy, Chernogolovka (RU)

(73) Assignees: Globetek 2000 Pty Ltd, Brighton (AU); The Federal State Autonomous Educational Institution of the Higher Professional Education "National University of Science and Technology", Moscow (RU)

( * ) Notice: Subject to any disclaimer, the term of this patent is extended or adjusted under 35 U.S.C. 154(b) by 211 days.

(21) Appl. No.: 14/366,136

(22) PCT Filed: Oct. 18, 2012

(86) PCT No.: PCT/RU2012/000840
§ 371 (c)(1),
(2) Date: Jun. 17, 2014

(87) PCT Pub. No.: WO2013/095188
PCT Pub. Date: Jun. 27, 2013

(65) Prior Publication Data
US 2015/0342769 A1      Dec. 3, 2015

(30) Foreign Application Priority Data
Dec. 19, 2011  (RU) .............................. 2011151657

(51) Int. Cl.
*A61B 1/273* (2006.01)
*A61F 2/958* (2013.01)
(Continued)

(52) U.S. Cl.
CPC .......... *A61B 1/273* (2013.01); *A61B 1/00082* (2013.01); *A61B 1/31* (2013.01); *A61F 2/958* (2013.01); *A61F 2002/045* (2013.01)

(58) Field of Classification Search
CPC ......... A61B 1/273; A61B 1/2736; A61B 1/31; A61B 1/0082; A61B 1/00082; A61F 2/82;
(Continued)

(56) References Cited

U.S. PATENT DOCUMENTS 5,292,321 A * 3/1994 Lee .................. A61B 17/22
606/198
5,571,135 A * 11/1996 Fraser .................. A61F 2/95
606/198
(Continued)

FOREIGN PATENT DOCUMENTS

RU         2180528 C2       3/2002

OTHER PUBLICATIONS

Wikipedia. Double-balloon enteroscopy. Feb. 26, 2009. Accessed Mar. 3, 2016. https://web.archive.org/web/20090226051709/http://en.wikipedia.org/wiki/Double-balloon_enteroscopy.*
(Continued)

*Primary Examiner* — Ryan J Severson
*Assistant Examiner* — Charles Wei
(74) *Attorney, Agent, or Firm* — Brinks Gilson & Lione

(57) ABSTRACT

This invention relates to medicine, more specifically, to the surgical treatment of intestinal obstructions using the minimum invasive (endoscopic) method. The invention provides the possibility of the surgical treatment of intestinal obstructions along the entire length of the intestine by means of stenting. The technical result achieved by the first and second subjects of the invention is providing the total surgical treatment of intestinal obstructions in the narrow and large intestine by installing a stent at an intestine obstruction location in a manner allowing further moving (Continued)

the stent during its positioning or removal and avoiding damage to the intestine as a result of the surgical manipulations. Said technical objective is achieved with the first subject of the invention, i.e. the method, as follows. The method of surgical treatment of intestinal obstructions in narrow and large intestine comprises the movement of the endoscope across the entire length of the narrow and large intestine and delivering the dilatation balloon and stent system to the obstructed section of the intestine. After the dilatation balloon and stent system is delivered to the obstructed section of the intestine, the dilatation balloon is installed at the intestine obstruction location, and the normal intestine section is restored by inflating the dilatation balloon. Then the volume of the dilatation balloon is reduced, the balloon is retracted to the endoscope, and the stent is installed at the intestine obstruction location. The movement of the dilatation balloon and stent is controlled using a hydraulic piston mechanism. Said technical objective is achieved with the second subject of the invention, i.e. the device, as follows. The endoscope for the total surgical treatment of intestinal obstructions in narrow and large intestine comprises a hydraulic endoscope movement drive and an endoscope case installed in the outer tube. Said endoscope case comprises channels for the supply of gas and liquid into the intestine cavity, an optical channel, a light channel and two manipulation channels. The stent is installed at the distal end of one of said manipulation channels at the central portion of the manipulation shaft which is rigidly mounted on the stern extension piston and has stopping balloons at both ends. The distal end of the other manipulation channel comprises the dilatation balloon mounted on a hollowed manipulation shaft which in turn is rigidly mounted on the dilatation balloon extension piston. The proximal ends of said manipulation channels comprise hydraulic piston mechanisms acting on said dilatation balloon extension piston and on said stent extension piston. Said dilatation balloon and said stent stopping balloons are connected via said gas supply channels to said hydraulic piston mechanisms installed at the proximal ends of said manipulation channels.

20 Claims, 2 Drawing Sheets

(51) Int. Cl.
  *A61B 1/00* (2006.01)
  *A61B 1/31* (2006.01)
  *A61F 2/04* (2013.01)
(58) Field of Classification Search
  CPC ...... A61F 2/95; A61F 2/958; A61F 2002/821; A61F 2002/9583; A61F 2002/011; A61F 2002/9517; A61F 2002/9586; A61F 2002/9505; A61F 2002/9665; A61M 25/0113; A61M 25/0155
  USPC ..... 606/191, 197; 623/1.11, 1.23, 26, 23.64, 623/23.7, 23.65
  See application file for complete search history.

(56) References Cited

U.S. PATENT DOCUMENTS

| | | | | |
|---|---|---|---|---|
| 5,800,520 | A * | 9/1998 | Fogarty | A61F 2/07 606/194 |
| 6,129,755 | A * | 10/2000 | Mathis | A61F 2/91 623/1.15 |
| 6,146,389 | A * | 11/2000 | Geitz | A61F 2/95 600/121 |
| 6,858,005 | B2 | 2/2005 | Ohline et al. | |
| 6,945,989 | B1 * | 9/2005 | Betelia | A61F 2/95 623/1.11 |
| 7,033,384 | B2 * | 4/2006 | Gannoe | A61F 2/04 128/898 |
| 2002/0013616 | A1 * | 1/2002 | Carter | A61F 2/07 623/1.15 |
| 2007/0038283 | A1 * | 2/2007 | Mustapha | A61F 2/856 623/1.11 |
| 2007/0112355 | A1 * | 5/2007 | Salahieh | A61F 2/2418 606/108 |
| 2007/0287886 | A1 * | 12/2007 | Saadat | A61B 1/0008 600/115 |
| 2008/0177142 | A1 * | 7/2008 | Roskopf | A61B 1/00082 600/115 |

OTHER PUBLICATIONS

Endo-Flex, Instruktsii po ekspluatatsii samorasshiryayuschikhsya nitinolovykh stentov, Nov. 29, 2010, retrieved from the Internet (http://www.endo-flex.ru/content/instru_stents.pdf).
Chaika, Yu A., et al., Endovaskulyarnoe stentirovanie, Zhurnal "Meditsinkskie novosti," 2005, No. 5, retrieved from the Internet (http://www.mednovosti.by/journal.aspx?article=909).
Loginov, A.S., et al., Osobennosti endoskopicheskogo issledovaniya pri porazheniyakh toschei I podvzdoshnoi kishki, Rossiiskiy Gastroenterologicheskiy zhurnal, 2000, No. 2, retrieved from the Internet (http://medi.ru/Doc/6700205.htm).
Kuo Nagasako M.D., Differentsialnaya diagnostika zabolevaniy pryamoi i obodochnoi kishki, Apr. 27, 2006, retrieved from the internet (http://medi.ru/DOC/6700205.htm).
Peirs, J., et al., Design of miniature parallel manipulators for integration in a self-propelling endoscope, Sensors and Actuators 85 (2000), pp. 409-417.
International Search Report, for corresponding International application No. PCT/RU2012/000840, dated Apr. 11, 2013.

* cited by examiner

METHOD OF SURGICAL TREATMENT OF INTESTINAL OBSTRUCTIONS IN NARROW AND LARGE INTESTINE AND DEVICE FOR ITS IMPLEMENTATION

CROSS-REFERENCE TO RELATED APPLICATIONS

This application is a National Stage application of PCT International Application No. PCT/RU2012/000840, filed Oct. 18, 2012, which claims priority to RU 2011151657, filed Dec. 19, 2011, the entire contents of which are hereby incorporated by reference herein.

FIELD OF THE INVENTION

This invention relates to medicine, more specifically, to the surgical treatment of intestinal obstructions using the minimum invasive (endoscopic) method. The invention provides the possibility of the surgical treatment of intestinal obstructions along the entire length of the intestine by means of stenting.

BACKGROUND

The surgical treatment of small intestine diseases is limited by the possibility of access to the target zone and is therefore carried out within a limited space of the intestine. General surgeries are carried out for the examination of the upper part of the gastrointestinal tract (up to 1.5 m in depth), the access being limited by the duodenum. Conventional colonoscopy also allows treating intestinal obstructions up to 2 m in depth of the large intestine. The rest portion of the small intestine the total length of which with the esophagus is up to 10 m remains inaccessible for noninvasive stenting. Capsule endoscopy is often used for the examination of the entire gastrointestinal tract, but it does not allow surgery.

The only solution for small intestine obstruction patients are abdominal operations which include extensive laparotomy and hence the related risks and complications.

Known are an examination and diagnostic method for the gastrointestinal tract, more specifically, the small intestine, and an ultra-long (10 m) endoscope for the implementation of said method (U.S. Pat. No. 7,481,764 B2, publ. 21 Jan. 2009). Said known method and device provide an efficient tool for the total navigation of the gastrointestinal tract along its entire length.

Disadvantages of said known method and device are that they do not allow small intestine surgery by means of minimum invasive access.

The closest counterpart of the method and device disclosed herein are the method of surgical treatment of empty tubular bodies including blood vessels, arteries and veins, and a device for the implementation of said method (RU 2388433 C2, publ. 10 May 2010). In accordance with this technical solution, the obstructed section of an empty tubular body is expanded with an expandable medical implant for providing support to the tubular body cavity. This implant relates to a specific type of medical components called stents. Stents are delivered to the obstructed area of a vessel by means of special systems including dilatation balloons.

Disadvantages of said known method and device are that they do not allow delivering and installing a stent via an endoscope to any area along the length of the small intestine. The only solution for small intestine obstruction patients, many of who are above 60, are abdominal operations which include extensive laparotomy and hence the related risks and complications.

The prior attempts of providing endoscopes allowing total diagnostics and treatment of small intestine have not been clinically successful. For many years an unresolved problem has been to overcome friction across the entire length of the small intestine due to its extensive tortuosity and up to 10 m length.

SUMMARY

The object of this invention is to provide for total surgical treatment of intestinal obstructions of small and large intestine by installing a stent at an intestine obstruction location in a manner allowing further moving the stent during its positioning or removal and avoiding damage to the intestine as a result of the surgical manipulations.

Said technical objective is achieved with the first subject of the invention, i.e. the method, as follows.

The method of surgical treatment of intestinal obstructions in small and large intestine comprises the movement of the endoscope across the entire length of the small and large intestine and delivering the dilatation balloon and stent system to the obstructed section of the intestine. After the dilatation balloon and stent system is delivered to the obstructed section of the intestine, the dilatation balloon is installed at the intestine obstruction location, and the normal intestine section is restored by inflating the dilatation balloon. Then the volume of the dilatation balloon is reduced, the balloon is retracted to the endoscope, and the stent is installed at the intestine obstruction location. The movement of the dilatation balloon and stent is controlled using a hydraulic piston mechanism.

Furthermore, the endoscope can be moved across the entire length of the small and large intestine via the oral cavity or the anal orifice.

Said technical objective is achieved with the second subject of the invention, i.e. the device, as follows.

The endoscope for the total surgical treatment of intestinal obstructions in small and large intestine comprises a hydraulic endoscope movement drive and an endoscope case installed in the outer tube. Said endoscope case comprises channels for the supply of gas and liquid into the intestine cavity, an optical channel, a light channel and two manipulation channels.

The stent is installed at the distal end of one of said manipulation channels at the central portion of the manipulation shaft which is rigidly mounted on the stent extension piston and has stopping balloons at both ends.

The distal end of the other manipulation channel comprises the dilatation balloon mounted on a hollowed manipulation shaft which in turn is rigidly mounted on the dilatation balloon extension piston. The proximal ends of said manipulation channels comprise hydraulic piston mechanisms acting on said dilatation balloon extension piston and on said stent extension piston. Said dilatation balloon and said stent stopping balloons are connected via said gas supply channels to said hydraulic piston mechanisms installed at the proximal ends of said manipulation channels.

Said dilatation balloon and said stent are mounted on hollowed manipulation shafts in a detachable manner.

The distal ends of said manipulation channels further comprise springs that enhance the back stroke of said dilatation balloon extension piston and said stent extension piston.

Said stent is secured in its expanded and compressed positions by means of threads made of biologically soluble materials.

Said threads are secured to the stent with a securing means made from fast soluble non-toxic biodegradable glue.

BRIEF DESCRIPTION OF THE DRAWINGS

This invention will be exemplified with a drawing where.

DETAILED DESCRIPTION

Figure 1:
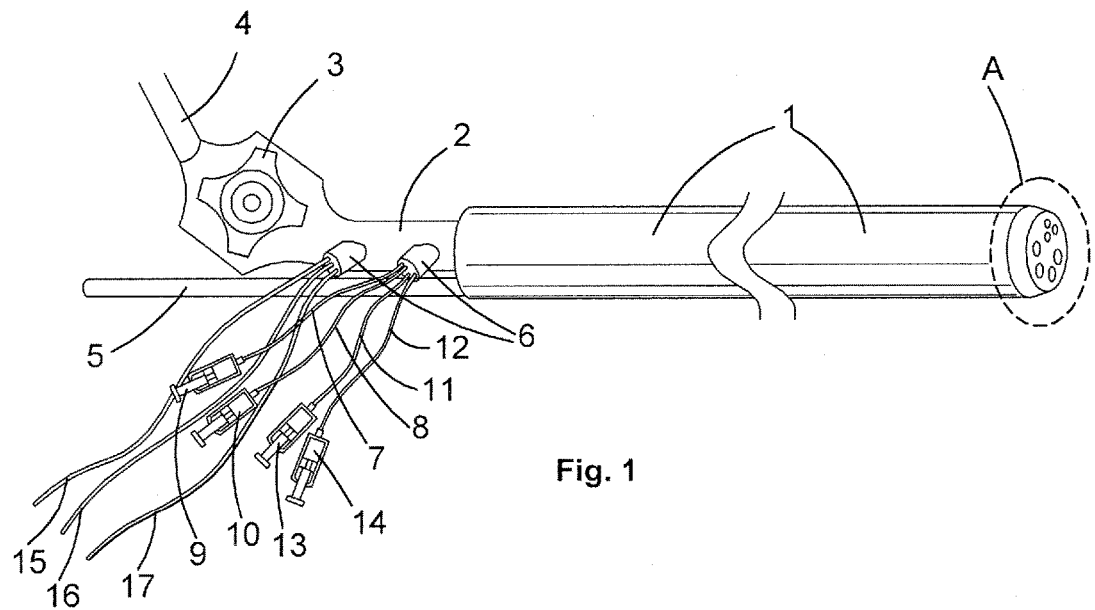
FIG. 1 shows the general view of the endoscope.
Figure 2:
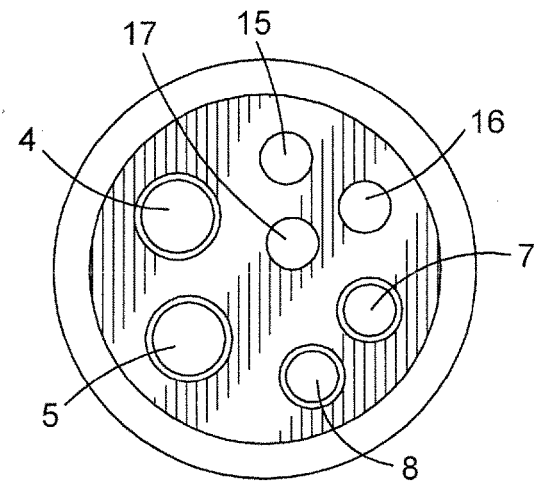
FIG. 2 shows the frontal view of the distal end of the endoscope (Section A in FIG. 1)
Figure 3:
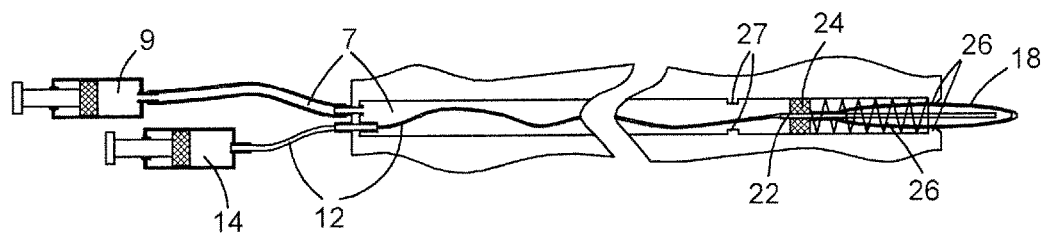
FIGS. 3 and 4 show longitudinal sections of the manipulation channels and
FIG. 5 shows the design and mounting of the stent.
Figure 4:
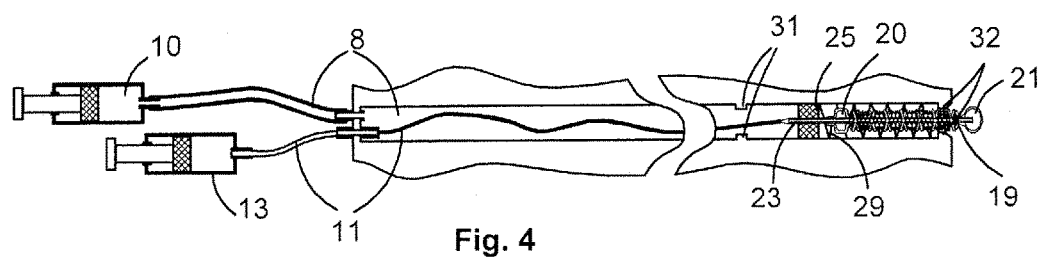
Figure 5:
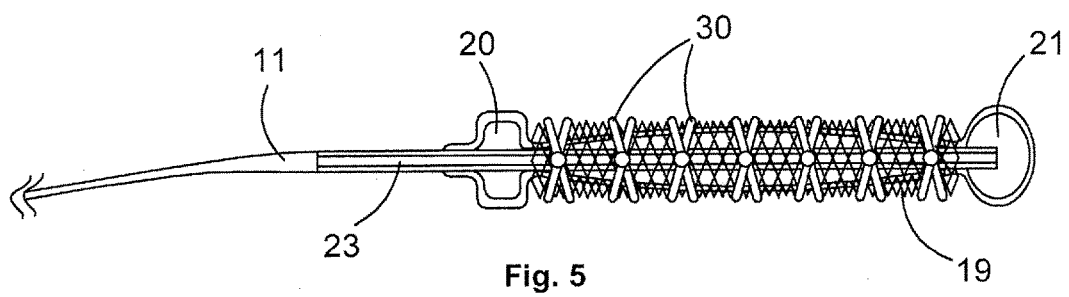

The endoscope comprises (FIGS. 1-5) an outer tube 1, an endoscope case 2, a distal endoscope end rotation mechanism 3, an optical channel 4, a hydraulic drive tube 5, a port 6, a dilatation balloon manipulation channel 7, a stem manipulation channel 8, a hydraulic piston mechanism 9 that produces pressure in the channel 7, a hydraulic piston mechanism 10 that produces pressure in the channel 8, a channel 11 for gas supply to the end balloons 20 and 21, a channel 12 for gas supply to the dilatation balloon 18, a pneumatic piston mechanism 13, a pneumatic piston mechanism 14, a channel 15 for liquid supply to the intestine, a light guide 16, a channel 17 for gas supply to the intestine, a dilatation balloon 18, a stent 19, a rear end balloon 20, a front end balloon 21, a manipulation shaft 22 of the dilatation balloon 18, a manipulation shaft 23 of the stent 19, a piston 24 for the extension of the dilatation balloon 18, a piston 25 for the extension of the stent 19, a spring 26 for the back stroke of the piston 24, a rear limiter 27 of the back stroke of the piston 24, a front limiter 28 of the back stroke of the piston 24, a spring 29 for the back stroke of the piston 25, a threads 30 for holding the stent 19, a rear limiter 31 of the back stroke of the piston 25 and a front limiter 32 of the back stroke of the piston 25.

The method according to this invention is implemented using said device as follows.

During the surgical treatment of intestinal obstructions in small and large intestine the outer tube 1 is moved across the entire length of the small and large intestine by the action of the hydraulic drive comprised in the tube 5. The total movement of the endoscope and the delivery of the dilatation balloon and stent system to the obstruction section of the intestine are carried out through the oral cavity or through the anal orifice. The endoscope is 3.5-10 m in length.

After the dilatation balloon and stent system is delivered to the obstruction section of the intestine, the normal intestine section in the obstruction location is restored. To this end, positive pressure is applied to the manipulation channel 7 by means of the hydraulic piston mechanism 9 mounted on the proximal end of the endoscope, said pressure being transmitted to the piston 24. The piston 24 extends the dilatation balloon 18 mounted on the manipulation shaft 22 to the obstruction location.

After the dilatation balloon 18 is delivered to the obstruction location, gas is delivered to its volume via the channel 12 from the pneumatic piston mechanism 13 to inflate the dilatation balloon 18 thus widening the obstructed portion and restoring the normal section of the intestine.

Then the dilatation balloon 18 is deflated by applying negative pressure to its volume via the channel 12 from the pneumatic piston mechanism 13 and retracted back into the manipulation channel 7.

The back movement of the balloon 18 can be enhanced by the spring 26 mounted in the distal end of the endoscope to facilitate the retraction of the balloon 18 into the manipulation channel 7.

Then the stent is delivered to the widened obstructed portion of the intestine. initially, positive pressure is applied to the manipulation channel 8 by means of the hydraulic piston mechanism 10 mounted on the proximal end of the endoscope, said pressure being transmitted to the piston 25. The piston 24 extends the stent 25 mounted on the manipulation shaft 23 to the obstruction location.

The stent 19 is secured in the desired longitudinal position by means of the front and rear end balloons 20 and 21 mounted on the manipulation shaft 23.

The manipulation shaft 23 can be made of polymer materials having sufficient elasticity, e.g. polymer.

The end balloons 20 and 21 are deployed and the stent 19 is secured in the desired longitudinal position by supplying gas from the pneumatic piston mechanism 14 via the channel 11 to the end balloons 20 and 21.

The stent 19 is secured in the compressed position by means of threads 30.

The stent 19, secured in the compressed position with the threads 30 and in the desired longitudinal position with the end balloons 20 and 21, is extended from the distal end of the endoscope by delivering positive pressure from the pneumatic piston mechanism 10 to the piston 25 by the distance equal to the piston stroke, i.e. 8-15 cm. The end balloons 20 and 21 also avoid damage to the intestine when the stent 19 is moved.

After the stent 19 is installed at the obstruction location, the glue dissolves (within 5 min after being extended from the endoscope). After the glue has dissolved, the threads 30 lose their ability to secure the stent 19 in the compressed position. As a result the stent expands in the obstruction location automatically, for example, due to the shape memory effect or its intrinsic elasticity which is typical of stents made, for example, of polymer materials, and restores the patency of the intestine.

After the stent 19 has expanded, the threads are pressed by the stent 19 to the intestine wall and secured in said position. The biodegrading composition of the threads reduces the time of foreign object presence in the intestine. The time of thread dissolution depends on the structure of its material and possible presence of a medicinal coating.

The end balloons 20 and 21 are deflated by applying negative pressure from the pneumatic piston mechanism 14 following which the shaft 23 is retracted from the obstruction location to the channel 8.

The back movement of the shaft 23 can be enhanced by the spring 29 mounted in the distal end of the endoscope to facilitate the retraction of the stent 19 into the manipulation channel 8.

The pneumatic piston mechanisms 13 and 14 may contain gas of various density, and the hydraulic piston mechanisms 9 and 10 may contain liquid of various specific weight depending on endoscope length. Longer endoscopes require higher density (specific weight) of liquid.

What is claimed is:
1. A method of surgical treatment of intestinal obstructions in a small or large intestine by moving an endoscope through the small or large intestine and delivering a dilata- tion balloon and stent system to an obstructed section of the intestine, the method comprising:
using an endoscope comprising:
an endoscope case;
a stent manipulation channel installed in the endoscope case;
a stent manipulation shaft installed at a distal end of the stent manipulation channel, the stent manipulation shaft being fixed on a stent extension piston;
stopping balloons attached to each end of the stent manipulation shaft;
a dilatation balloon manipulation channel installed in the endoscope case;
a dilatation balloon mounted on a dilatation balloon manipulation shaft installed at a distal end of the dilatation balloon manipulation channel, the dilatation balloon manipulation shaft being fixed on a on a dilatation balloon extension piston; and
a hydraulic piston mechanism installed at proximal ends of the stent manipulation channel and the dilatation balloon manipulation channel, the hydraulic piston mechanism being configured to act on the dilatation balloon extension piston and the stent extension piston via gas supply channels connected between the hydraulic piston mechanism and each of the dilatation balloon extension piston and the stent extension pistons;
installing the dilatation balloon at the obstructed section of the intestine,
restoring the diameter of the obstructed section by inflating the dilatation balloon,
reducing the volume of the dilatation balloon,
retracting the balloon to the endoscope, and
installing a stent at the obstructed section of the intestine,
wherein the installing of the dilatation balloon and the stent is controlled using the hydraulic piston mechanism.

2. The method of claim 1 wherein the endoscope is moved through the small or large intestine via the oral cavity or the anal orifice.

3. The method of claim 1, further comprising deflating the dilatation balloon before delivering the dilatation balloon and stent system to the obstructed section of the intestine.

4. The method of claim 1, further comprising securing the stent in a desired longitudinal position using front and rear end balloons.

5. The method of claim 1, further comprising;
securing said stent in its expanded and compressed positions by means of threads made of biologically soluble materials and wherein said threads are secured to the stent with a securing means made from fast soluble non-toxic biodegradable glue; and
automatically expanding the stent when the glue dissolves.

6. The method of claim 5, further comprising pressing and securing the threads to the intestine wall after the stent expands.

7. An endoscope for the total surgical treatment of intestinal obstructions in small or large intestine comprising a hydraulic endoscope movement drive and an endoscope case installed in an outer tube, said endoscope case comprising supply channels for the supply of gas and liquid into an intestine cavity, an optical channel, a light channel and two manipulation channels, a stent being installed at the distal end of one of said manipulation channels at a central portion of a manipulation shaft which is fixed on a stent extension piston and has stopping balloons at both ends, and the distal end of the other manipulation channel comprising a dilatation balloon mounted on a hollowed manipulation shaft which in turn is fixed on a dilatation balloon extension piston, wherein proximal ends of said manipulation channels comprise hydraulic piston mechanisms acting on said dilatation balloon extension piston and on said stent extension piston, and said dilatation balloon and said stent stopping balloons are connected via said gas supply channels to said hydraulic piston mechanisms installed at the proximal ends of said manipulation channels.

8. The endoscope of claim 7 wherein said dilatation balloon and said stent are mounted on the hollowed manipulation shafts in a detachable manner.

9. The endoscope of claim 7 wherein the distal ends of said manipulation channels further comprise springs that enhance the back stroke of said dilatation balloon extension piston and said stent extension piston.

10. The endoscope of claim 9, further comprising at least one of a rear limiter and a front limiter for the back stroke of at least one of the dilatation balloon extension piston and the stent extension piston.

11. The endoscope of claim 7 wherein said stent is secured in its compressed position by means of threads made of biologically soluble materials.

12. The endoscope of claim 11 wherein said threads are secured to the stent with a securing means made from fast soluble non-toxic biodegradable glue.

13. An endoscope for deploying a stent in a small or large intestine, the endoscope comprising:
an endoscope case;
a stent manipulation channel installed in the endoscope case;
a stent manipulation shaft installed at a distal end of the stent manipulation channel, the stent manipulation shaft being fixed on a stent extension piston;
stopping balloons attached to each end of the stent manipulation shaft;
a dilatation balloon manipulation channel installed in the endoscope case;
a dilatation balloon mounted on a dilatation balloon manipulation shaft installed at a distal end of the dilatation balloon manipulation channel, the dilatation balloon manipulation shaft being fixed on a dilatation balloon extension piston; and
a hydraulic piston mechanism installed at proximal ends of the stent manipulation channel and the dilatation balloon manipulation channel, the hydraulic piston mechanism being configured to act on the dilatation balloon extension piston and the stent extension piston via gas supply channels connected between the hydraulic piston mechanism and each of the dilatation balloon extension piston and the stent extension piston.

14. The endoscope of claim 13, further comprising channels installed in the endoscope case for supplying gas and liquid into an intestine cavity.

15. The endoscope of claim 13, further comprising an optical channel installed in the endoscope case.

16. The endoscope of claim 13, further comprising a light channel installed in the endoscope case.

17. The endoscope of claim 13, wherein the dilatation balloon and the stent are mounted on the manipulation shafts in a detachable manner.

18. The endoscope of claim 13, wherein the distal ends of the manipulation channels further comprise springs that enhance the back stroke of the dilatation balloon extension piston and the stent extension piston.

19. The endoscope of claim 13, wherein the stent is secured in a compressed position by means of threads made of biologically soluble materials.

20. The endoscope of claim 19, wherein the threads are secured to the stent with a securing means made from fast soluble non-toxic biodegradable glue.

\* \* \* \* \*

UNITED STATES PATENT AND TRADEMARK OFFICE
CERTIFICATE OF CORRECTION

PATENT NO. : 10,080,489 B2
APPLICATION NO. : 14/366136
DATED : September 25, 2018
INVENTOR(S) : Elena Prokopievna Ryklina et al.

It is certified that error appears in the above-identified patent and that said Letters Patent is hereby corrected as shown below:

On the Title Page

Item (71) Applicants, delete "The Federal State Autonomous Educational Institution of the Higher Professional Education National" and insert in its place --The Federal State Autonomous Educational Institution of the Higther Professional Education "National University of Science and Technology"--

Item (57) Abstract, page 2, Line 29, delete "stern" and insert in its place --stent--

Signed and Sealed this
Twenty-fifth Day of December, 2018

Andrei Iancu
*Director of the United States Patent and Trademark Office*